(12) United States Patent
Lee

(10) Patent No.: US 6,603,268 B2
(45) Date of Patent: Aug. 5, 2003

(54) METHOD AND APPARATUS FOR REDUCING OZONE OUTPUT FROM ION WIND DEVICES

(75) Inventor: Jim L. Lee, Rohnert Park, CA (US)

(73) Assignee: Zenion Industries, Inc., Rohnert Park, CA (US)

( * ) Notice: Subject to any disclaimer, the term of this patent is extended or adjusted under 35 U.S.C. 154(b) by 0 days.

(21) Appl. No.: 10/168,724

(22) PCT Filed: Dec. 22, 2000

(86) PCT No.: PCT/US00/35402

§ 371 (c)(1),
(2), (4) Date: Jun. 21, 2002

(87) PCT Pub. No.: WO01/48781

PCT Pub. Date: Jul. 5, 2001

(65) Prior Publication Data

US 2002/0195951 A1 Dec. 26, 2002

Related U.S. Application Data

(60) Provisional application No. 60/173,075, filed on Dec. 24, 1999.

(51) Int. Cl.$^7$ .............................................. H05B 31/36
(52) U.S. Cl. ................................... 315/111.01; 156/345
(58) Field of Search ....................... 315/111.01, 111.24, 315/111.51; 156/345, 643.1; 134/1; 313/74; 331/94.5

(56) References Cited

U.S. PATENT DOCUMENTS 3,702,973 A  *  11/1972  Daugherty et al. ...... 315/111.01
5,938,854 A  *   8/1999  Roth .......................... 156/345

* cited by examiner

*Primary Examiner*—Don Wong
*Assistant Examiner*—Jimmy T. Vu
(74) *Attorney, Agent, or Firm*—Larry D. Johnson; Craig M. Stainbrook; Johnson & Stainbrook, LLP

(57) ABSTRACT

Ozone output in ion wind devices using one or more emitters (10) and an array of collectors (20) (accelerators) may be reduced through catalytic conversion of the produced ozone back to oxygen by using various materials placed in or downstream from the airflow, such as a manganese dioxide coating on the accelerator substrate elements. Precious metal or activated carbon coatings may also be used for the purpose of converting ozone to oxygen.

10 Claims, 2 Drawing Sheets

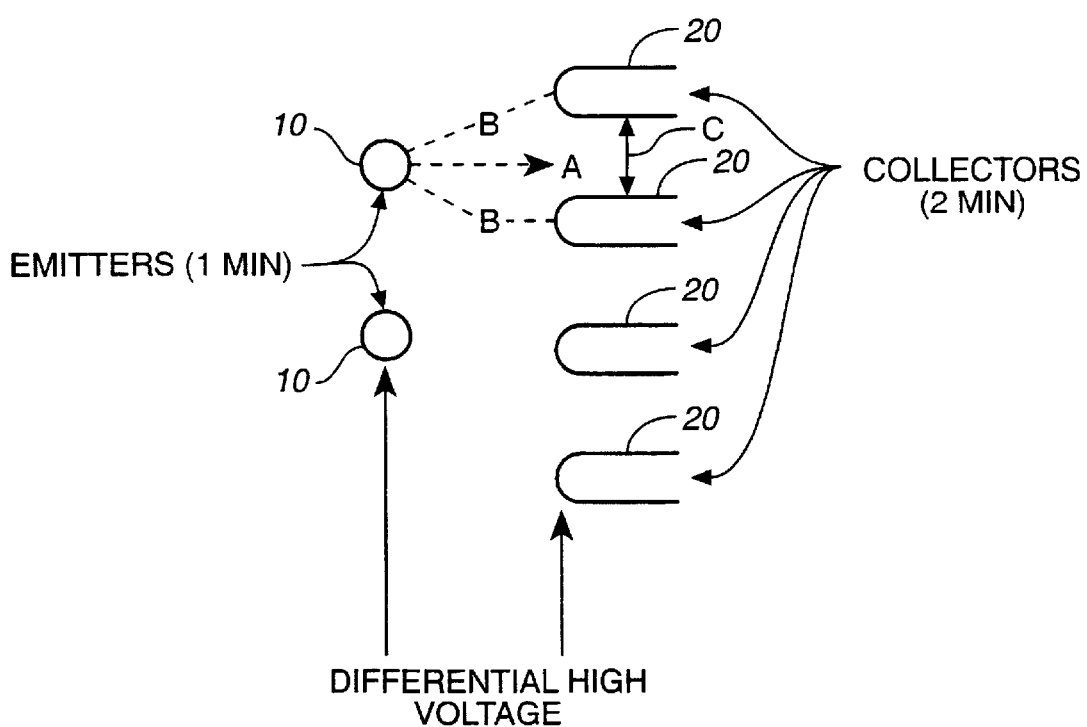
FIG._1

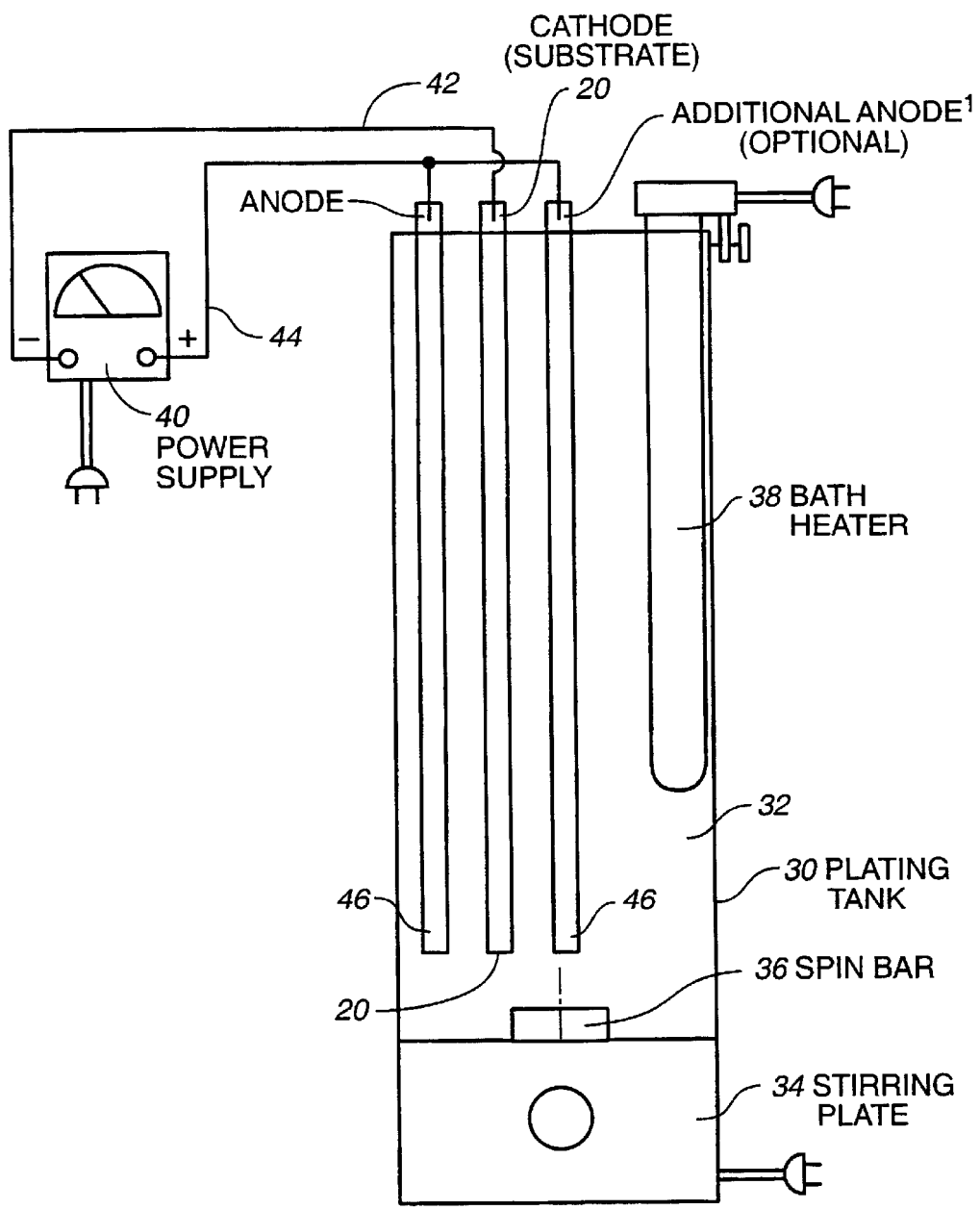
FIG._2

METHOD AND APPARATUS FOR REDUCING OZONE OUTPUT FROM ION WIND DEVICES

This application claims the benefit of Provisional application Ser. No. 60/173,075 filed Dec. 24, 1999.

BACKGROUND OF THE INVENTION

1. Technical Field

This invention relates generally to ion generators and ion wind devices, and more specifically to an improved method and apparatus for reducing the ozone output from ion wind devices.

2. Background Art

Ion wind devices such as described in Lee U.S. Pat. No. 4,789,801 provide accelerated gas ions through the use of differential high voltage electric fields between one or more emitters and an array of collectors (accelerators). The ions are entrained in the ambient bulk gases, causing the gases to flow. Gas velocities can reach as high as eight hundred feet per minute. However, the high voltage electric fields used to generate the gas ions and provide the force necessary for gas acceleration are also responsible for creating molecular dissociation reactions, the most common of which include ozone generated from oxygen when such devices are operating in a breathable atmosphere. It is an object of this invention to provide methods to reduce the ozone output by converting the produced ozone back to oxygen.

The U.S. Food and Drug Administration has determined that indoor airborne ozone in concentrations above 50 ppb (parts per billion) may be hazardous to humans. NIOSH has ruled that indoor concentrations of ozone above 100 ppb may be hazardous to humans. Devices which utilize high voltage electric fields to generate atmospheric plasma, corona discharge and air ions are all susceptible to generating the allotrope, ozone. There exist a linear relationship between the level of the high voltage fields and current and the level of ozone concentration in most direct current operated ion wind systems. Also, a linear relationship exists between the acceleration velocity and intensity of the electric fields (typically the higher the voltage the higher the acceleration). Since it is desired to have maximum acceleration, methods must be employed to limit or eliminate unwanted ozone output.

DISCLOSURE OF INVENTION

When ozone is produced in ion wind devices it may be converted back to oxygen by using various materials placed in or downstream from the airflow. Noble metals such as gold, silver or platinum may be plated to the leading edge (or the entire surface) of the accelerator array substrate to function as a catalytic converter to convert the ozone to oxygen. However, precious metal plating may not be a practical method of catalyzing ozone due to the high cost of the precious metal material itself. Accordingly, the invention discloses a method to plate manganese dioxide onto accelerator substrate elements which also reduces, through catalytic conversion, ozone levels. The $MnO_2$ coating will catalyze ozone to from $O_2$ ($O_3$–$O_2$) thus reducing ozone from the airflow. Activated carbon coatings may also be used for the purpose of converting ozone to oxygen.

The disclosed manganese plating and oxidation process has proven successful in reducing by greater than 20% the concentration of ozone downstream from the primary emissivity source.

BRIEF DESCRIPTION OF THE DRAWINGS

FIG. 1 is a schematic view of an emitter and accelerator array of an ion wind device; and FIG. 2 is a side elevation view of an apparatus for plating manganese to an accelerator substrate.

BEST MODE FOR CARRYING OUT THE INVENTION

FIG. 1 is a schematic view of a typical ion wind array. The emitter or emitters 10 are typically constructed of 0.1 mm pure tungsten wire and may be of any length. The collectors (also referred to as accelerators) 20 are typically constructed of any non corrosive conductive material such as copper, aluminum, stainless steel, or brass. The emitter 10 is always located opposite and at the center (A) of the opening of the accelerators 20. The equidistant (B) of the emitter to the leading edge (radius) of the accelerators 20 may vary depending upon desired operational effect, but is typically one inch. This is also true of the spacing (C) between accelerators.

The differential voltage applied across the array must be at least 6,500 volts in order to effect any substantial ion mobility and subsequent airflow. Typical configurations consist of applying a positive high voltage to the emitter and a negative high voltage to the collector to achieve a maximum differential voltage of 15,000 volts D.C. These voltage potentials may be reversed, however, when this is done an uneven plasma envelope is developed at the emitter source, which results in excessive production of corona noise and ozone production. The array may be driven by a single positive or a single negative high voltage excitation source to the emitter with the collectors having a high impedance return to ground (to reduce load current and breakover arcing). Also, the excitation voltage may be modulated in ways taught in U.S. Pat. No. 4,789,801 to achieve desired results.

FIG. 2 is a side elevation view of an apparatus for plating manganese to an accelerator substrate 20. Plating tank 30 is filled with a solution 32 of manganese sulfate, ammonium sulfate, and EDTA in distilled water, and mixed a with magnetic stirring plate 34 and spin bar 36. Bath heater 38 may be used to maintain the bath temperature at 40 degrees C. Power supply 40 negative lead 42 is connected to accelerator substrate 20, and positive lead 44 is connected to one or more manganese plates or rods 46, and the substrate and manganese rods are placed in the plating tank 30. The power supply is energized for an appropriate period to plate a desired layer of manganese onto the substrate 20. After the plating process, the manganese coating on the substrate is oxidized as by immersion in a hydrogen peroxide solution.

Procedural guidelines for the plating process may include the following:

1.0 Purpose: Preparation of a plating bath for manganese, the plating of that metal onto a substrate, and the oxidation of the metal coating.

2.0 Definitions
  2.1 Substrate: Object which is to be plated.

3.0 Equipment and Supplies
  3.1 Laboratory scale, triple beam balance (accuracy+/−0.05 gram).
  3.2 Magnetic stirring plate.
  3.3 Magnetic spin bar.
  3.4 Plating tank, glass cylinder (approximately 5 inches in diameter and 13 inches long).
  3.5 Plating bath heater (e.g., aquarium heater approximately 100 watts).

3.6 Distilled water.
3.7 Manganese sulfate $MnSO_4$ $2H_2O$.
3.8 Ammonium sulfate $(NH_4)_2$ $SO_4$
3.9 EDTA, disodium (ethylenediaminetetraacetate).
3.10 Manganese rods or plate (12 inches in length).
3.11 Electrical leads (3 feet in length with alligator clips 20 watt minimum capacity).
3.12 Power supply (D.C. 0 to 20 watts capacity with current meter).
3.13 Substrate (see definition 2.1).
3.14 Water rinse (container holding sufficient water to completely immerse the substrate).
3.15 Oxidation container (container holding sufficient hydrogen peroxide solution, 10% to completely immerse the substrate).
3.16 Hydrogen peroxide (any concentration at or above 10%).
3.17 Plating bath storage bottles (glass 1 liter).
3.18 Sulfuric acid container (container holding sufficient sulfuric acid solution, 10%, to completely immerse the substrate).
3.19 Sulfuric acid (any concentration at or above 10%).
3.20 10% sulfuric acid storage bottle (glass 1 liter).
3.21 10% hydrogen peroxide storage bottle (glass 1 liter).
3.22 Graduated cylinder (plastic 100 ml capacity).

4.0 Plating Bath Preparation
4.1 Place the plating tank (3.4) on the magnetic stirring plate (3.2) and place the magnetic spin bar (3.3) inside the plating tank.
4.2 Add 2.0 liters of distilled water (3.6) to the plating tank and turn on the magnetic stirring plate. Set the speed indicator to "5".
4.3 Using the laboratory scale (3.1) weight out 200 grams of manganese sulfate (3.7) and gradually add it to the water in the plating tank.
4.4 When all of the manganese sulfate has been dissolved, weigh out and gradually add 150 grams of ammonium sulfate (3.8) to the solution in the plating tank.
4.5 When all of the ammonium sulfate has been dissolved weigh out and gradually add 60 grams EDTA (3.9).
4.6 When all of the EDTA has been dissolved, add additional distilled water so that the total volume of the plating solution fills the plating tank to ½ inch from the top of the tank.
4.7 The plating bath will have a red or pink tint when freshly mixed but will soon clear and assume a gold tint as plating continues. An insoluble white precipitate will form from the fresh solution and settle out. This precipitate can be removed from the plating bath by decanting the clear bath after the precipitant has settled.

5.0 Plating Procedure
5.1 With the plating bath in the plating tank, place the plating bath heater (3.5) in the plating tank and turn it on. Adjust the heater so the bath temperature is maintained at 40° C.
5.2 Substrate (3.13) is cleaned by polishing with steel wool and scrubbing with a cloth or paper towel and soap and water. Don't touch the substrate with uncovered fingers after rinsing.
5.3 Fill the sulfuric acid container (3.18) with sufficient sulfuric acid (3.19) solution (10%) to allow immersion of the substrate.
Solution: A 10% sulfuric acid solution is used to reduce (remove oxygen from) the surface of the substrate. The 10% acid solution can be prepared from acid concentration of greater than 10% by dilution with distilled water. An example of dilution follows: Using 60% sulfuric acid, make a 10% solution. Measure out 100 ml of 60% acid using a graduated cylinder. This volume of acid solution contains 60 ML of pure sulfuric acid and 50 ml of water. Using the following equation solve for "x" the volume of water to mix with the 60% acid solution:

$$\frac{\text{Volume of pure acid}}{\text{Volume of acid solution} + X} = .10$$

$$\frac{60 \text{ ml}}{100 \text{ ml} + X \text{ ml}} = .10$$

$$\frac{60 \text{ ml}}{.10} = 100 + X$$

$$600 - 100 = X = 500 \text{ ml}$$

Measure out 500 ml of distilled water and place it in the sulfuric acid container. Add the 100 ml of 60% sulfuric acid slowly while mixing. Never add water to acid, always add acid (AAA) to water. The 10% acid solution may be stored in a glass storage bottle (3.20) when not in use. The acid solution is used at room temperature.
5.4 Immerse the substrate in the sulfuric acid solution for 2 to 5 minutes.
5.5 Rinse the substrate in a running stream of water for 1 minute. Do not dry the substrate or touch it with uncovered fingers after rinsing.
5.6 Connect the electrical leads (3.11) to the power supply (3.12) and connect the positive (+) electrical lead to a manganese rod or plate (3.10). Additional anodes, arranged symmetrically around the substrate, can be used to improve the uniformity of the coating. Connect the negative lead (−) to the substrate (3.13).
5.7 Set the power supply output to the desired current and place the rod (anode) and substrate (cathode) into the plating tank. The electrical lead end of the anode should not contact the plating bath as this might cause contamination. The electrical lead end of the cathode can be in the plating bath as it will just be coated with manganese. See FIG. 1.
Current: Desired plating current will vary directly with the amount of substrate surface area. A ratio can be defined which expresses the relationship of current to surface area. This ratio is called the current density and has units of amps/area where the area is in units of square inches or square meters. The current density is a constant of the plating process and is used to calculate the desired current for any size substrate.
Experiments indicate that a current density of 1.25 amps/square inch works very well for this process. An example calcution of the desired plating current for a substrate follows: Calculate the desired plating current for a copper rod 0.125 inches in diameter and 11 inches in length.
The surface area of the rod is: (0.125 in.) (3.14) (11 in.)=4.32 square inches
The desired plating current is: (4.32 sq. in.) (1.25 amps/sq. In.)=5.4 amps
5.8 Turn on the power supply for the desired amount of time. It will be observed that gas is liberated at both the anode and cathode. These gases are hydrogen (at the cathode) and oxygen (at the anode). They are not toxic but being mixed above the plating tank produces a condition of possible combustion so care must be taken not to ignite them (no smoking, open flame, or sparks in the vicinity).

Time: Desired plating time will vary with the desired coating thickness. Using the current density indicated in note 2, a uniform thin coating can be obtained in 1 minute. Plating for 5 minutes will result in an intermediate thickness while plating for 10 to 15 minutes will give a thick metal coating to the substrate.

5.9 After plating is complete, remove the substrate from the plating bath and immerse it in the water rinse (3.14) then turn off the power supply. This sequence preserves the metal coating from degradation by the plating bath. The bath will attack manganese metal, using the metal ion to replace the ammonium ion in solution. The anode rod should also be removed from the solution when the power is off.

6.0 Storage 6.1 The plating bath can be stored and reused many times as the manganese will be replenished in solution by the manganese anodes. Some precipitate will form during plating and this will settle out of solution during storage.

6.2 Store the plating bath storage bottles (3.17) when it is not used. The shelf life of the plating bath should be unlimited. Add distilled water if necessary to make up for evaporation and decomposition of water during plating.

7.0 Oxidation Procedure 7.1 Fill the oxidation container (3.15) with sufficient hydrogen peroxide (3.16) solution (10%) to allow immersion of the coated substrate.

Solution: A 10% hydrogen peroxide solution is used to oxidize the manganese coating on the substrates. The 10% hydrogen peroxide solution can be prepared from hydrogen peroxide concentrations of greater than 10% by dilution with distilled water. The dilution of a hydrogen peroxide solution follows exactly the procedure used for the dilution of a sulfuric acid solution explained in section 5.10. The only difference being that the sulfuric acid is replaced by hydrogen peroxide. The hydrogen peroxide solution is used at room temperature.

7.2 Immerse the coated substrate in the hydrogen peroxide solution for 20 minutes. Oxygen gas will be liberated during this process so care should be taken to remove all sources of ignition from the vicinity.

7.3 Rinse the coated substrate in water to remove all hydrogen peroxide solution. A running stream of water or the water rinse (3.14) may be used.

8.0 Safety 8.1 Good chemical safety procedures should be used at all times in this process as it involves the use of hazardous materials.

What is claimed as invention is:

1. A method for reducing ozone output from ion wind devices, said method comprising the steps of:

providing an emitter;

providing a plurality of collectors, plating said collectors with a substance adapted to react with ozone to form oxygen; and positioning said collectors generally equidistant from said emitter in an ion wind device, wherein when the ion wind device operates, said substance reacts with ozone to form oxygen and reduce ozone output.

2. The method of claim 1 wherein said step of plating said collectors comprises plating with manganese dioxide.

3. The method of claim 2 wherein said step of plating said collectors comprises:

providing a plating tank filled with a solution of manganese sulfate and ammonium sulfate in distilled water;

providing a power supply having a positive lead and a negative lead;

connecting said negative lead to a collector to form a cathode, and connecting said positive lead to a manganese plate to form an anode;

placing said cathode and anode in said solution; and energizing said power supply to plate said cathode with manganese.

4. The method of claim 3 further including the step of oxidizing said manganese plating.

5. The method of claim 1 wherein said step of plating said collectors comprises plating with a precious metal material.

6. The method of claim 1 wherein said step of plating said collectors comprises plating with activated carbon.

7. An ion wind device comprising:

an emitter;

a plurality of collectors positioned generally equidistant from said emitter, said collectors at least partially coated with a substance adapted to react with ozone to form oxygen, whereby when the ion wind device operates, said substance reacts with ozone to form oxygen and reduce ozone output.

8. The ion wind device of claim 7 wherein said substance comprises manganese dioxide.

9. The ion wind device of claim 7 wherein said substance comprises a precious metal.

10. The ion wind device of claim 7 wherein said substance comprises activated carbon.

* * * * *